US012797176B2

(12) United States Patent
Egnelöv et al.

(10) Patent No.: US 12,797,176 B2
(45) **Date of Patent: *Nov. 17, 2026**

(54) MESH SUPPORT DEVICE FOR A BREAST IMPLANT AND A METHOD FOR FIXATING A BREAST IMPLANT IN A MESH SUPPORT DEVICE

(71) Applicant: NOVUS SCIENTIFIC AB, Uppsala (SE)

(72) Inventors: Per Egnelöv, Uppsala (SE); Wasana Egnelöv, Uppsala (SE)

(73) Assignee: NOVUS SCIENTIFIC AB, Uppsala (SE)

( * ) Notice: Subject to any disclaimer, the term of this patent is extended or adjusted under 35 U.S.C. 154(b) by 680 days.

This patent is subject to a terminal disclaimer.

(21) Appl. No.: 17/764,820

(22) PCT Filed: Sep. 28, 2020

(86) PCT No.: PCT/EP2020/077026

§ 371 (c)(1),
(2) Date: Mar. 29, 2022

(87) PCT Pub. No.: WO2021/063850

PCT Pub. Date: Apr. 8, 2021

(65) Prior Publication Data

US 2022/0338971 A1 Oct. 27, 2022

(30) Foreign Application Priority Data

Oct. 3, 2019 (SE) .................................... 1951126-0

(51) Int. Cl.
*A61F 2/00* (2006.01)
*A61F 2/12* (2006.01)

(52) U.S. Cl.
CPC .............. *A61F 2/0063* (2013.01); *A61F 2/12* (2013.01); *A61F 2210/0004* (2013.01); *A61F 2220/0033* (2013.01); *A61F 2250/003* (2013.01)

(58) Field of Classification Search
CPC .................. A61F 2/0045; A61F 2/0063; A61F 2002/0068; A61F 2/12; A61F 2220/003; A61F 2250/003
(Continued)

(56) References Cited

U.S. PATENT DOCUMENTS 6,015,428 A * 1/2000 Pagedas ............... A61B 17/062 606/232
7,875,074 B2 1/2011 Chen et al.
(Continued)

FOREIGN PATENT DOCUMENTS

EP 2 002 800 A1 12/2008
EP 3 085 337 A1 10/2016
(Continued)

OTHER PUBLICATIONS

Swedish Search Report, Application No. 1951126-0, Mar. 30, 2020, 2 pages.
(Continued)

*Primary Examiner* — Kathleen S Holwerda
(74) *Attorney, Agent, or Firm* — Foley & Lardner LLP

(57) ABSTRACT

The invention relates to a mesh support device (10) for supporting abreast implant (40), wherein the mesh support device (10) comprises a first panel (11) and a second panel (12), of which at least the second panel (12) is a mesh panel (12), which consists of a large number of individual meshes, and wherein the mesh support device (10) further comprises a first arm (31), which has a length Li and is arranged at a first side of the first panel (11), and a second arm (32), which
(Continued)

has a length L2 and is arranged at a second side of the first panel (11), the second side being opposite to the first side, wherein each of the first and second arms (31, 32) is configured to be threaded through anyone of said large number of individual meshes and the lengths $L_1$ and $L_2$ are chosen such that 30 mm <$L_1$ <210 mm and 30 mm <$L_2$ <210 mm. The invention also relates to a method for fixating the breast implant (40) in the support device (10).

18 Claims, 5 Drawing Sheets

(58) Field of Classification Search
USPC .......................................................... 606/151
See application file for complete search history.

(56) References Cited

U.S. PATENT DOCUMENTS

| | | | | |
|---|---|---|---|---|
| 8,016,841 | B2 | 9/2011 | Magnusson et al. | |
| 8,083,755 | B2 | 12/2011 | Mathisen et al. | |
| 9,566,370 | B2 | 2/2017 | Mathisen et al. | |
| 9,782,245 | B2 * | 10/2017 | Mujwid | A61F 2/0045 |
| 2006/0142786 | A1 * | 6/2006 | Mathisen | A61L 31/129 606/151 |
| 2008/0021265 | A1 | 1/2008 | Garbin et al. | |
| 2008/0161837 | A1 * | 7/2008 | Toso | A61F 2/0045 606/151 |
| 2009/0082864 | A1 | 3/2009 | Chen et al. | |
| 2009/0318752 | A1 * | 12/2009 | Evans | A61F 2/0045 600/37 |
| 2010/0023029 | A1 | 1/2010 | Young | |
| 2010/0234679 | A1 * | 9/2010 | Evans | A61F 2/0045 600/37 |
| 2012/0185041 | A1 | 7/2012 | Mortarino et al. | |
| 2013/0304098 | A1 | 11/2013 | Mortarino | |
| 2014/0088344 | A1 | 3/2014 | Mujwid et al. | |
| 2016/0331504 | A1 * | 11/2016 | Wang | A61B 90/02 |
| 2020/0222177 | A1 * | 7/2020 | Paydar | A61F 2/12 |
| 2020/0345476 | A1 * | 11/2020 | Wang | A61L 27/362 |

FOREIGN PATENT DOCUMENTS

| | | | |
|---|---|---|---|
| WO | WO 2008/042434 | A2 | 4/2008 |
| WO | WO 2009/017680 | A2 | 2/2009 |
| WO | WO 2014/149096 | A1 | 9/2014 |
| WO | WO 2016/144885 | A1 | 9/2016 |

OTHER PUBLICATIONS

Swedish Search Report, Application No. 1951127-8, Apr. 1, 2020.
Non-Final Office Action issued in U.S. Appl. No. 17/765,560 on Apr. 28, 2025.
Final Office Action issued in U.S. Appl. No. 17/765,560 on Aug. 18, 2025.

* cited by examiner

MESH SUPPORT DEVICE FOR A BREAST IMPLANT AND A METHOD FOR FIXATING A BREAST IMPLANT IN A MESH SUPPORT DEVICE

Field of the Invention

The present invention relates generally to a medical support device for supporting a medical implant and relates particularly to a support device for supporting a breast implant, wherein the support device is a mesh support device comprising a first panel and a second panel, of which panels at least the second panel is a mesh panel, which is composed of a large number of individual meshes, and further comprising at least two arms arranged at the first panel, wherein each arm is relatively long and is configured to be forced and threaded through anyone of said individual meshes. The invention also relates to a method for fixating a breast implant in such a mesh support device.

BACKGROUND OF THE INVENTION

A medical breast reconstruction is a medical procedure that typically involves the use of prosthetic breast implants, e.g. silicone or saline implants, which, during the medical procedure, are positioned either inside or outside the breast muscle, to recreate a female breast. Within the art of reconstructive and cosmetic breast surgery, it is further common to combine the breast implant with a support device, which is arranged to at least partly enclose the breast implant. The support device can then be attached, e.g. stitched, to the human breast tissue to thereby fixate the position of the breast implant, or the support device can simply provide a structure for facilitating and promoting tissue integration of the breast implant.

Support devices for breast implants are available in many types and designs but are typically made from a mesh material and have a flat back wall and a concave front wall. The mesh material used can be a permanent mesh material or can be made from a biodegradable material. Support devices of this type are, for example, disclosed in the U.S. Pat. No. 7,875,074 to Chen et al., wherein the support devices comprise a concave receiving space, which is defined by a back wall and a front wall for at least partly receiving and supporting a breast implant therein.

A common feature of the known support devices for breast implants is that they provide a pocket in which the breast implant is to be placed. However, breast implants come in several sizes and also shapes, which means that several support devices having pockets with corresponding sizes and shapes must be kept in store, which in itself poses a logistical problem, not least since a support device, which often is made from a bio-degradable material, typically has an expiry date that must not be exceeded.

In the published U.S. patent application Ser. No. 2013/0304098 to Mortarino, which relates to a three-dimensional fabric structure in the form of a pocket, in which a breast implant is to be placed, it is in one embodiment described how the three- dimensional fabric structure may be created by means of a first mesh panel, which comprises a number of small tabs that are arranged to be inserted into corresponding slots in a second mesh panel, whereupon the tabs are sutured to the second mesh panel. The first and second mesh panels are, by a doctor or surgeon, created by imposing corresponding templates, having sizes proportional to the breast implant to be supported, over the mesh panels, and then trim to the mesh panels to the sizes and shapes of the templates.

Further, even if the size and shape of particular support device are well fitted to a specific breast implant, there is — typically due to the pocket-like shape — always a certain mismatch between the round or more or less hemi-spherically shaped breast implant and the outer rim area of the receiving pocket, i.e. the breast implant does not completely fill out the space where a back wall of the support device meets the front wall, which makes it difficult to exactly position the breast implant. Furthermore, many existing support devices for breast implants are by doctors and surgeons perceived to have a design that is too elaborated to be optimal from a medical perspective, i.e. the support devices require extra attention and special handling before and/or during the implantation procedure. Needless to say, any medical device which has a design that is not optimal from a medical perspective implies a certain risk for the patient.

Although a support device according to the prior art may serve its intended purpose well, it is still accompanied by problems related to its adaption to the size and shape of the breast implant that is to be supported by the support device in question. The known support devices are typically also associated with disadvantages when it comes to user-friendliness, i.e. how easy they are to handle by doctors and surgeons before or during an implantation procedure. A general object of the present invention is therefore to provide an improved support device for a breast implant, which support device has a design and shape that adapt to the size and shape of the breast implant and which can be easily adapted to a span of different implant sizes and shapes. Another object of the invention is to provide an improved support device which is easy to handle during a medical implantation procedure. A further object of the invention is to provide a mesh support device having a design that is easy to manufacture. A still further object of the invention is to present a method for fixating a medical breast implant in a support device, by which method the support device can securely fixate a large span of implant sizes and shapes.

SUMMARY OF THE INVENTION

The above-mentioned objects are achieved by the present invention according to the independent claims. Preferred embodiments are set forth in the dependent claims.

The present invention relates to a mesh support device for supporting a breast implant, wherein the mesh support device comprises a first panel and a second panel, of which first and second panels at least the second panel is a mesh panel, which consists of a large number of individual meshes, and wherein the mesh support device further comprises a first arm, which has a length $L_1$ and is arranged at a first side of the first panel, and a second arm, which has a length $L_2$ and is arranged at a second side of the first panel, the second side being opposite to the first side, wherein each of the first and second arms is configured to be threaded through anyone of said large number of individual meshes. As will be further explained below, the lengths Li and L2 are such that 30 mm $\le L_1 \le$ 210 mm, and more preferably 70 mm $\le L_1 \le$ 180 mm, and most preferably 110 mm $\le L_1 \le$ 150 mm; and 30 mm $\le L_2 \le$ 210 mm, and more preferably 70 mm $\le L_2 \le$ 180 mm, and most preferably 110 mm $\le L_2 \le$ 150 mm.

For all embodiments presented herein, also the first panel can be a mesh panel, and also the first and second arms can be made from mesh material.

Thus, an important feature of the present mesh support device is that a doctor or surgeon during a medical breast implant procedure can first thread the first arm through anyone of the individual meshes of the second mesh panel and then thread the second arm through anyone of the remaining individual meshes of the second mesh panel. In practice, the doctor or surgeon selects an individual mesh that is located at a suitable position on a first lateral side of the breast implant to be supported by the mesh support device and selects an individual mesh that is located at a suitable position on a second and opposite lateral side of the breast implant to be supported by the mesh support, such that, when the first arm has been threaded through the individual mesh located on the first lateral side and the second arm has been threaded through the individual mesh located on the second lateral side, the breast implant is positioned between the first arm and the second arm, and, when the first and second arms have been tightened, the breast implant is securely fixated in this position. By the configuration of the first and second arms such that they can be threaded through anyone of the individual meshes of the second mesh panel, the doctor or surgeon can easily choose individual meshes located at suitable positions and thread the first and second arms therethrough, such that a particular mesh support having a given configuration in terms of size and shape can accommodate and fixate breast implants with large spans of sizes and shapes. Further, for manufacturing reasons it is preferred that also the first panel is a mesh panel, which further can be made from the same mesh as the second mesh panel, as will be described below.

The invention relates also to a method for positioning and fixating a breast implant in a mesh support device comprising a first panel and second panel, which are configured to be positioned opposite each other and of which at least the second panel is a mesh panel, which consists of a large number of individual meshes, wherein the mesh support device further comprises a first arm arranged at a first side of the first panel and a second arm arranged at a second side of the first panel, the second side being opposite to the first side, which method comprises the steps of:

- determining a suitable position for the breast implant between the first panel and the second mesh panel;
- based on the determined suitable position, selecting a first one of said large number of individual meshes and threading the first arm through this selected first individual mesh; and
- based on the determined suitable position, selecting a second one of said large number of individual meshes and threading the second arm through this selected second individual mesh, wherein the selected first individual mesh and the selected second individual mesh are selected such that the breast implant is positioned between the first arm and the second arm.

As used herein, “a mesh” is a web or net construction made from threads, mono- filaments or multi-filaments. The mesh comprises a large number of “individual meshes”. An “individual mesh” as used herein comprises an aperture as well as the threads, mono-filaments or multi-filaments being located most adjacent to the aperture, i.e. the closest surrounding threads, mono-filaments or multi-filaments. The perimeter of the aperture is defined by the most adjacent, i.e. the closest surrounding, threads, mono-filaments or multi-filaments. The shape and size of the aperture are given by the pattern(s) by which the mesh is manufactured, e.g. the knitting pattern or weaving pattern. It should further be appreciated that the aperture of an individual mesh can be, and most likely will be, deformed, e.g. widened, during the threading of an arm therethrough. It can also happen that some of the threads, mono-filaments or multi-filaments that define the perimeter of an aperture of an individual mesh are damaged and even broken during the threading operation.

The individual meshes as referred to herein are nominally considerably smaller than the widths of the arms, and it should therefore be appreciated that the term “thread” as it is used herein includes some force and manipulation of the arms. An arm can, for example, be tightly rolled or folded along its longitudinal extension, to thereby obtain a thin and pointy object that can be forced and pushed through an individual mesh. According to embodiments of the invention, an arm can have a pointed profile. Alternatively, an arm can be manipulated by a threading device, such as a needle, a pair of tweezers or a pair of forceps, which can be utilized to force and push an arm through an individual mesh or, alternatively, pull an arm through an individual mesh. Thus, the term “threading an arm through an individual mesh” encompasses both “pushing an arm through an individual mesh” and “pulling an arm through an individual mesh”. Embodiments of the present method are directed to such manipulations of the arms of the mesh support device.

To provide for a support device which is easy to handle and which can accommodate breast implants having different shapes and sizes, it is, according to the invention, important that the first and second arms are relatively long and should, at the same time, not be excessively long, and it is therefore preferred that the lengths $L_1$ and $L_2$ are such that 30 mm$\leq L_1 \leq$210 mm, and more preferably 70 mm$\leq L_1 \leq$180 mm, and most preferably 110 mm$\leq L_1 \leq$150mm; and 30mm $\leq L_2 \leq$210 mm, and more preferably 70mm $\leq L_2 \leq$180mm, and most preferably 110mm $\leq L_2 \leq$150mm.

The first panel, which can be a mesh panel, and the second mesh panel are configured to lay or be arranged opposite to each other when assembled to encapsulate a breast implant; and by threading each of the arms of the first panel into selected and suitable located individual meshes of the second, opposite mesh panel, a space is created in which a breast implant is placed. With the breast implant in place between the first panel and the second mesh panel, the arms are tightened, i.e. the arms are pulled such that a larger portion of the respective length of the arm has passed through the individual mesh, and the breast implant is thereby firmly held in place between the first panel and the second mesh panel. The arms and the individual meshes have respective dimensions such that a friction locking is created between the inner contour of the individual mesh and the arm inserted therein, which prevents the arm from sliding back and out of the individual mesh. That is, the second mesh panel comprises a large number of individual meshes, where each individual mesh has an inner perimeter or configuration with at least one dimension that is smaller than a corresponding dimension of an arm that is arranged to be threaded through an individual mesh, such that a friction locking is created once the arm has been threaded through the individual mesh. The first mesh panel and the second mesh panel are preferably attached or connected to each other or the first mesh panel and the second mesh panel is made from a single piece preferably with a waist or a midsection separating the first and second mesh panel.

Here, it should be appreciated that according to the invention, each arm has a length that is relatively long, such that the arm is easy to handle for a doctor or surgeon, who threads the arm of a first panel into a selected individual mesh in a second mesh panel, i.e. the relatively long arm length provides by itself a user-friendliness since there is no need for the doctor to exactly determine how far the arm should be threaded through the selected individual mesh before the breast implant is in position between the panels. It is simply to thread a portion, e.g. a third or a half of the length, of each arm, place the breast implant in the space thereby created, and then tighten the arms, i.e. pull them further through the individual meshes. Further, by providing arms with relatively long lengths, a large interval of implant sizes and shapes can be accommodated within one size of the mesh support device, which eliminates or at least reduces the need for keeping a large variety of mesh support devices in store.

According to embodiments of the invention, a mesh support device can comprise more than two arms, such that a first panel or a second panel further comprises a third arm and a fourth arm.

For all embodiments of a mesh support device it is possible to arrange the mesh support device such that a first panel is made from a first material and a second mesh panel is made from a second material, the second material being different from the first material. In this case, the first and/or second materials can optionally be two bio- degradable materials having different degradation times. It may be preferred that both the first panel and the second panel are mesh panels, but to practice the present invention it is only mandatory that the second panel is a mesh panel, which is composed of a large number of individual meshes, through which the arms of the first panel can be threaded.

As an alternative, which also applies to all embodiments presented herein, a mesh support device can be arranged such that a first mesh panel and a second mesh panel are cut out from the same piece of mesh material, preferably with a waist dividing or separating the first mesh panel and the second mesh panel. In this case, the mesh support device can further be arranged such that also first and second arms are cut out from the same piece of mesh material. This feature provides for an efficient manufacturing of mesh support devices according to the invention, and to further provide for a material-saving manufacturing the mesh support device can be arranged such that a first arm extends generally along a first side of a first mesh panel and a second arm extends generally along a second, opposite side of the first mesh panel. Also, in these cases, the mesh material can be a bio-degradable mesh material.

BRIEF DESCRIPTION OF THE DRAWINGS

The invention will be described below with reference to the appended drawings, wherein same or similar elements have been given the same reference numerals, and.

DETAILED DESCRIPTION OF PREFERRED EMBODIMENTS

Figure 1A:
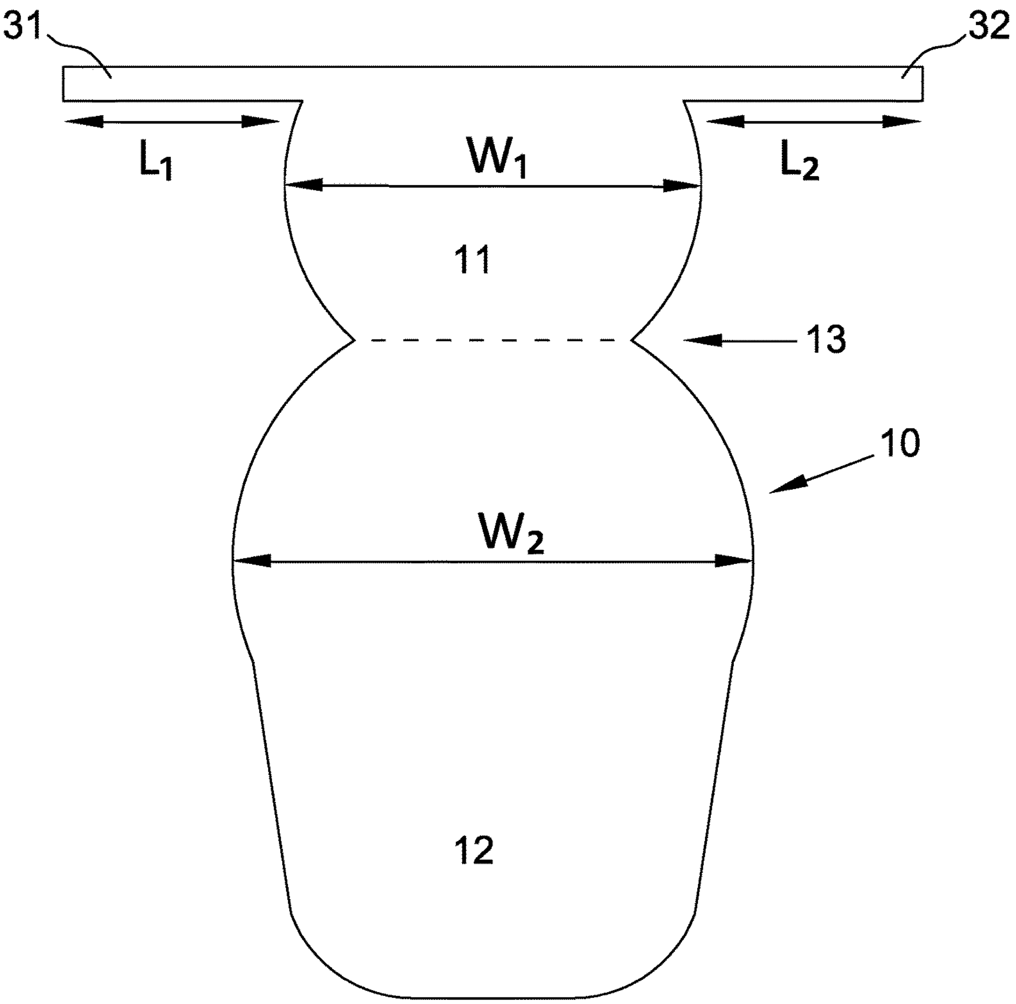
FIG. 1*a* illustrates schematically a front view of a first embodiment of a mesh support device according to the present invention.

In the figures, same, similar or corresponding elements have been given the same reference numerals.

FIG. 1*a* illustrates in front view a first embodiment of a mesh support device 10 according to the present invention. The mesh support device 10 comprises a first panel 11 having a largest width Wi and a second panel 12 having a largest width W2 and is in this particular embodiment larger, i.e. has a larger area, than the first panel 11. The second panel 12 is a mesh panel, which consists of a large number of individual meshes. The first panel 11, which also can be a mesh panel, is provided with a first arm 31, which extends out from the first panel 11 on a first side (on the left-hand side in FIG. 1*a*) of the first panel 11, and a second arm 32, which extends out from the first panel 11 on a second side (on the right-hand side in FIG. 1*a*) of the first panel 11, such that the arms 31, 32 project on opposite sides of the first panel 11. As will be discussed below, the first panel 11 and the second mesh panel 12 can have virtually any shape and are in this embodiment divided or separated (but not physically separated) by a waist or midsection 13. In one embodiment the first and the second arm are arranged essentially perpendicular to the first and second side respectively.

In one embodiment of the present invention the width of either the first mesh panel or the second mesh panel is larger than the other. In one embodiment the width of the first mesh panel is less than the width of the second mesh panel, $W_1<W_2$. In another embodiment of the present invention the area of either the first mesh panel or the second mesh panel is larger than the other. In one embodiment the area of the second mesh panel is larger than the area of the first mesh panel. This provides for a better enclosure of the breast implant and thereby better support.

Further, the first arm 31 has a length $L_1$ and the second arm 32 has length $L_2$. According to the invention, the arm lengths $L_1$ and $L_2$ are relatively long, and depend in practice on the size of the particular breast implant that the mesh support device 10 is intended to support. The size of the mesh support device 10, i.e. the areal size of the first panel 11 and the areal size of the second mesh panel 12, depends also on the size of the breast implant that is going to be used together with the support device 10, and here the size of the mesh support device 10 is characterized by the widths $W_1$ and $W_2$, respectively.

To achieve the special advantages with a mesh support device 10 according to the invention, the arms 31 and 32 are relatively long, but to not impair neither the user- friendliness nor the manufacturing efficiency should not be excessively long, and according to the present invention their lengths should be chosen such that 30mm≤$L_1$ ≤210mm, and more preferably 70mm ≤$L_1$ ≤180mm, and most preferably 110mm ≤$L_1$ ≤150mm; and 30mm ≤$L_2$ ≤210mm, and more preferably 70mm≤$L_2$ ≤180mm, and most preferably 110mm ≤$L_2$ ≤150mm. In this particular embodiment, there are two arms 31 and 32 provided on the first panel 11, but — as will be seen below — more arms, e.g. four or six arms, could be arranged. The first arm 31 and the second arm 32 have typically the same length ($L_1=L_2$), but it is within the scope of the invention that the lengths $L_1$ and $L_2$ are different ($L_1 \neq L_2$) as long as $L_1$ and $L_2$ fulfill their respective length intervals as given above.

Figure 1B:
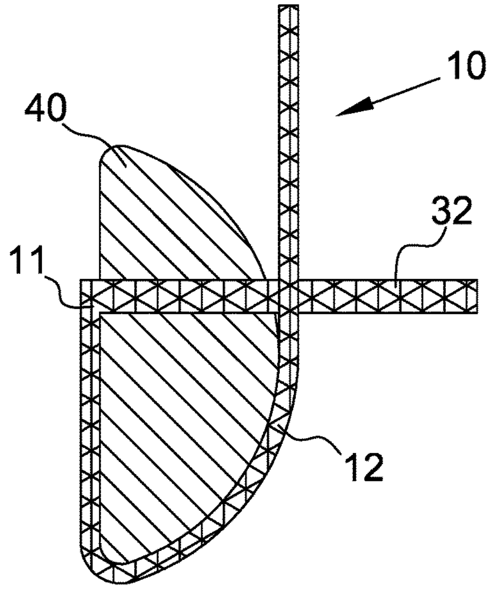
FIG. 1*b* illustrates in sideview a breast implant placed in the mesh support device of FIG. 1*a* in a first phase.

In FIG. 1*b*, the mesh support device 10 is schematically illustrated in sideview with a breast implant 40 positioned between the second mesh panel 12 and the first panel 11, which here is illustrated as the first mesh panel 11 but which can be made from a non- mesh material; and it can in particular be seen that the first and second panels 11, 12 have been brought to lay opposite each other such that a receiving space has been created therebetween. In practice, the mesh support device 10 has been gently folded or bent at the waist or midsection 13 such that the first panel 11 and the second mesh panels 12 have been moved to a position opposite each other. With the first and second panels 11, 12 in an opposite configuration, the first arm 31 has then been threaded through a first selected individual mesh of the second mesh panel 12 and the second arm 32 has been threaded through a second selected individual mesh of the second mesh panel 12 such that a space has been created between the first panel 11 and the second mesh panel 12, in which space the breast implant 40 has been placed. By providing relatively long arms 31, 32, it is easy for a doctor to first thread, e.g., the first arm 31 into and partly through the selected first individual mesh, and then thread the second arm 32 into and partly through the selected second individual mesh without risking that the first arm 31 during the subsequent operation retracts back out from the first selected individual mesh. By providing long arms 31, 32, a large variety of breast implant sizes can be accommodated and supported with one size of a mesh support device. The long arms 31, 32 also provide extra material, which can be mesh material, that can be attached and anchored, e.g. by sewing or stitching, to a patient's breast tissue, as will be thoroughly discussed in conjunction with FIG. 5 below.

Figure 1C:
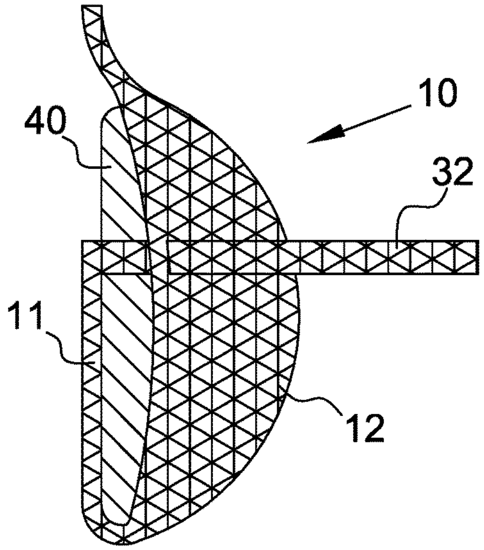
FIG. 1*c* illustrates the breast implant and the mesh support device in a second phase.

In the configuration shown in FIG. 1*b*, the arms 31, 32 have only been threaded a certain, limited distance through the respective individual meshes, e.g. a third or one half of the length of an arm can have been brought through an individual mesh, such that a spacious receiving space is created, in which it is easy to place the breast implant 40. In FIG. 1*c*, a subsequent configuration is shown, where the arms 31, 32 have been tightened around the breast implant 40, i.e. the arms 31, 32 have been threaded further through the respective individual meshes, such that major portions of the lengths $L_1$ and $L_2$ have passed the first selected individual mesh and the second selected individual mesh, respectively. By this tightening operation, the second mesh panel 12 is draped over and encloses the breast implant 40, which thereby is firmly held in place by the mesh support device 10.

Further, to keep the breast implant 40 securely in place, the first arm 31 and the second arm 32 are dimensioned such that a friction locking is created once one arm 31 or 32 has been threaded through an individual mesh. Thus, the widths of the first and second arms 31, 32 are chosen much larger than any dimension of an individual mesh. In practice, an arm 31 or 32 can be gently folded or rolled around its longitudinal axis before its outer end is threaded and forced through an individual mesh, which, when the arm 31 or 32 thereafter strives to resume its original shape, creates the friction locking that prevents the arm 31 or 32 from moving back out from the selected individual mesh once it has been threaded therethrough. To provide for a secure and reliable friction locking the first arm 31 can have width in the interval of 5 mm to 30 mm, and also the second arm 32 can have a width in the interval of 5 mm to 30 mm. However, the widths chosen for the first and second arms 31, 32 depend on the size and also shape of the individual meshes whose sizes and shapes are determined by the particular pattern the mesh is manufactured, e.g. the weaving pattern or knitting pattern which has been used during the manufacture of the second mesh panel 12 and, optionally, also the first mesh panel 11.

From FIGS. 1*b* and 1*c* it can further be inferred that the first panel 11 is a backside panel, which is intended to lay in contact with the flat backside of the breast implant 40. It can also be seen that the relatively larger area of the second mesh panel 12, which consequently is a frontside panel intended to be in contact with the convex frontside of the breast implant 40, ensures that the breast implant 40 is well covered and enclosed by the second mesh panel 12. Preferably the area of the second mesh panel 12 is so large that extra mesh material is provided around the outer rim of the breast implant 40, whereby the extra mesh material can be used for securing the support device 10 in the breast tissue of the human patient. This feature will be further described in conjunction with FIG. 5 below. In this embodiment, the first panel 11, which can be a mesh panel 11, has a generally circular shape with a top segment removed and a bottom segment removed, and the second mesh panel 12 has also a generally circular shape with a top segment removed and with a prolonged or extended bottom portion. The specific shapes of the first panel 11 and the second mesh panel 12 are, however, not overly important for practicing the present invention as long as a breast implant is sufficiently enclosed by the support device in question.

Figure 2A:
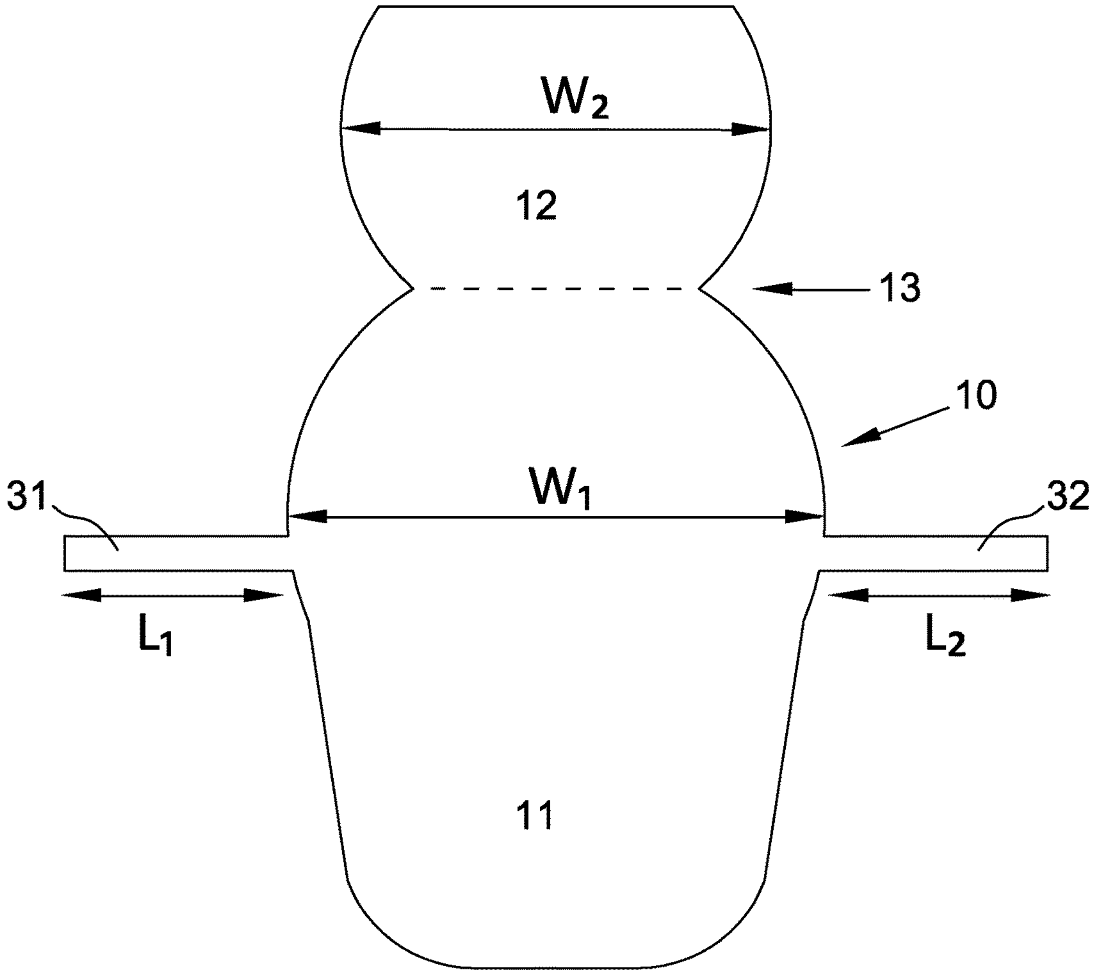
FIG. 2*a* illustrates schematically a front view of a second embodiment of a mesh support device according to the present invention.

FIG. 2*a* illustrates in front view a second embodiment of a mesh support device 10 according to the present invention. The mesh support device 10 comprises a first panel 11, which can be a mesh panel 11, having a largest width Wi and a second mesh panel 12 having a largest width $W_2$, where the second mesh panel 12 is composed of a large number of individual meshes and is in this particular embodiment smaller, i.e. has a smaller area, than the first panel 11. The first panel 11 is provided with a first arm 31, which extends out from the first panel 11 on a first side (on the left-hand side in FIG. 2*a*) of the first panel 11, and a second arm 32, which extends out from the first panel 11 on a second side (on the right-hand side in FIG. 2*a*) of the first panel 11, so that the arms 31, 32 project on opposite sides of the first panel 11. As will be discussed below, the first panel 11 and the second mesh panel 12 can have virtually any shape and are in this embodiment divided or separated (but not physically separated) by a waist or midsection 13.

Further, the first arm 31 has a length $L_1$ and the second arm 32 has length $L_2$. According to the invention, the arm lengths $L_1$ and $L_2$ are relatively long, and depend in practice on the size of the particular breast implant that the mesh support device 10 is intended to support. The size of the mesh support device 10, i.e. the areal size of the first panel 11 and the areal size of the second mesh panel 12, depends also on the size of the breast implant that is going to be used together with the support device 10, and here the size of the mesh support device 10 is characterized by widths $W_1$ and $W_2$, respectively.

To achieve the special advantages with a mesh support device 10 according to the invention, the arms 31 and 32 are relatively long, but to not impair neither the user- friendliness nor the manufacturing efficiency should not be excessively long, and according to the present invention their lengths should be chosen such that 30mm $L_1 \leq 210$mm, and more preferably 70mm $\leq L_1 \leq 180$mm, and most preferably 110mm$\leq L_1 \leq 150$mm; and 30mm $\leq L_2 \leq 210$mm, and more preferably 70mm$\leq L_2 \leq 180$mm, and most preferably 110mm $\leq L_2 \leq 150$mm. In this particular embodiment, there are two arms 31 and 32 provided on the first panel 11, but — as will be seen below — more arms, e.g. four or six arms, could be arranged. The first arm 31 and the second arm 32 have typically the same length ($L_1 = L_2$), but it is within the scope of the invention that the lengths $L_1$and $L_2$ are different ($L_1 \neq L_2$) as long as $L_1$ and $L_2$ fulfill their respective length intervals as given above.

Figure 2B:
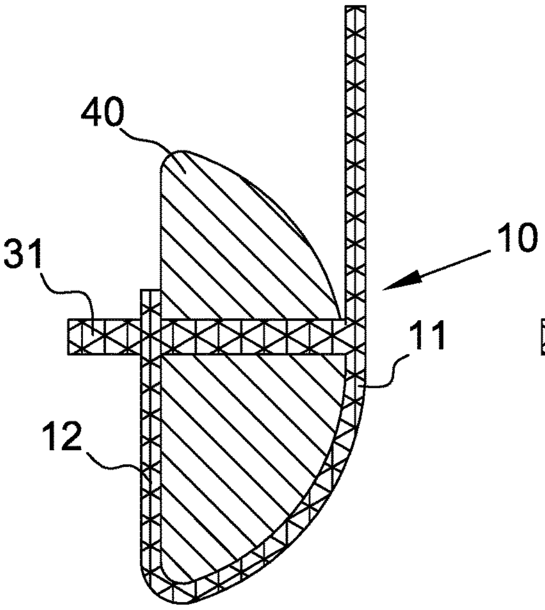
FIG. 2*b* illustrates in sideview a breast implant placed in the mesh support device of FIG. 2*a* in a first phase.

In FIG. 2*b*, the mesh support device 10 is schematically illustrated in sideview with a breast implant 40 positioned between the second mesh panel 12 and the first panel 11, which here is illustrated as the first mesh panel 11 but which can be made from a non- mesh material; and it can in particular be seen that the first and second panels 11, 12 have been brought to lay opposite each other such that a receiving space has been created therebetween. In practice, the mesh support device 10 has been gently folded or bent at the waist or midsection 13 such that the first panel 11 and the second mesh panel 12 have been moved to a position opposite each other. With the first and second panels 11, 12 in an opposite configuration, the first arm 31 has then been threaded through a selected first individual mesh of the second mesh panel 12 and the second arm 32 has been threaded through a selected second individual mesh of the second mesh panel 12, such that a space has been created between the first panel 11 and the second mesh panel 12, in which space the breast implant 40 has been placed. By providing relatively long arms 31, 32, it is easy for a doctor to first thread, e.g., the first arm 31 into and partly through the first selected individual mesh, and then thread the second arm 32 into and partly through the second selected individual mesh without risking that the first arm 31 during the subsequent operation retracts back out from the first selected individual mesh. By providing long arms 31, 32, a large variety of breast implant sizes can be accommodated and supported with one size of a mesh support device. The long arms 31, 32 also provide extra material, which can be mesh material, that can be attached and anchored, e.g. by sewing or stitching, to a patient's breast tissue, as will be thoroughly discussed in conjunction with FIG. 5.

Figure 2C:
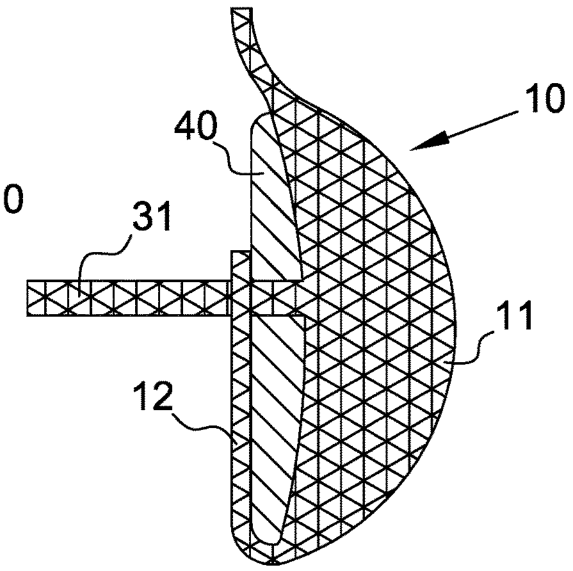
FIG. 2*c* illustrates the breast implant and the mesh support device in a second phase.

In the configuration shown in FIG. 2*b*, the arms 31, 32 have only been threaded a certain, limited distance through the respective selected individual meshes, e.g. a third or one half of the length of an arm can have been brought through a selected individual mesh, such that a spacious receiving space is created, in which it is easy to place the breast implant 40. In FIG. 2*c*, a subsequent configuration is shown, where the arms 31, 32 have been tightened around the breast implant 40, i.e. the arms 31, 32 have been threaded further through the selected individual meshes, such that major portions of the lengths $L_1$ and $L_2$ have passed the first selected individual mesh and the second selected individual mesh, respectively. By this tightening operation, the second mesh panel 12 is draped over and encloses the breast implant 40, which thereby is firmly held in place by the mesh support device 10.

Further, to keep the breast implant 40 securely in place, the first arm 31, i.e. the width thereof, and the second arm 32, i.e. the width thereof, and are dimensioned such that a friction locking is created once one arm 31 or 32 has been threaded through an individual mesh. In practice, an arm 31 or 32 can be gently folded or rolled around its longitudinal axis before its outer end is threaded through an individual mesh, something which, when the arm 31 or 32 thereafter strives to resume its original shape, creates the friction locking that prevents the arm 31 or 32 from moving back out from the individual mesh once it has been threaded therethrough. To provide for a secure and reliable friction locking the first arm 31 can have width in the interval of 5 mm to 30 mm, and also the second arm 32 can have a width in the interval of 5 mm to 30 mm. However, the widths chosen for the first and second arms 31, 32 depend on the sizes and also shapes of the individual meshes that constitute the second mesh panel 12.

From FIGS. 2*b* and 2*c* it can further be inferred that the second mesh panel 12 is a backside panel, which is intended to lay in contact with the essentially flat backside of the breast implant 40. It can also be seen that the relatively larger area of the first panel 11, which consequently is a frontside panel intended to be in contact with the convex frontside of the breast implant 40, ensures that the breast implant 40 is well covered and enclosed by the first panel 11. Preferably the area of the first panel 11 is so large that extra material, which can be mesh material, is provided around the outer rim of the breast implant 40, whereby the extra material can be used for securing the support device 10 in the breast tissue of the human patient. This feature will be further described in conjunction with FIG. 5 below. In this embodiment, the second mesh panel 12 has a generally circular shape with a top segment removed and a bottom segment removed, and the first panel 11 has also a generally circular shape with a top segment removed and with a prolonged or extended bottom portion. The specific shapes of the first panel 11 and the second mesh panel 12 are, however, not overly important for practicing the present invention as long as a breast implant is sufficiently enclosed by the support device in question.

A comparison of FIG. 1*a* and FIG. 2*a* reveals that according to the invention, the arms can be arranged at a first panel, which, when the support device is in use, either will constitute a front side or a backside, and that the individual meshes that compose a second mesh panel will, when the support device is in use, constitute the opposite and complementary side.

Figure 3:
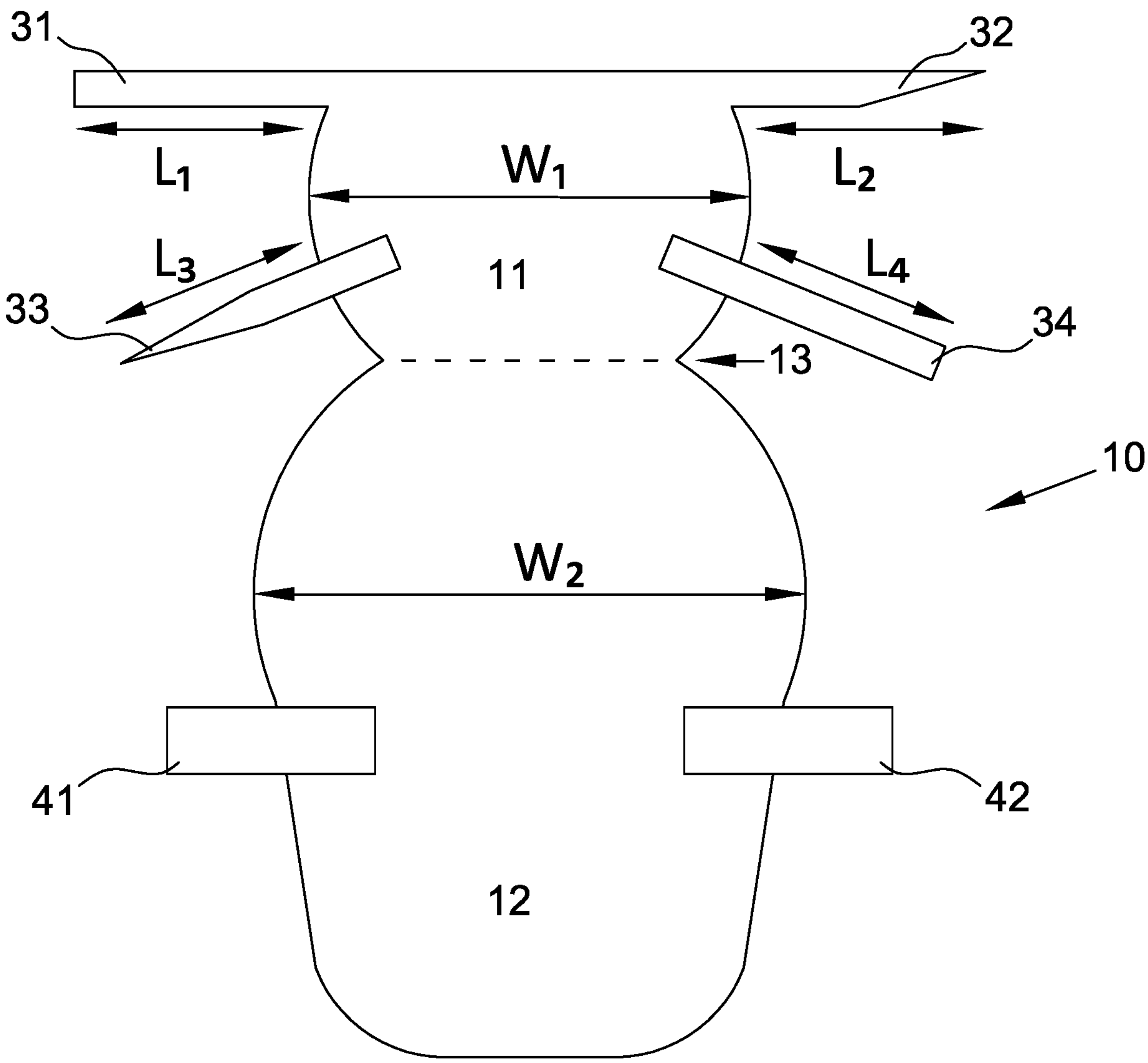
FIG. 3 illustrates schematically a front view of a third embodiment of a mesh support device according to the present invention.

FIG. 3 illustrates schematically a third embodiment of a mesh support device 10 according to the present invention. The mesh support device 10 comprises a first panel 11, which can be a first mesh panel 11, and a second mesh panel 12, where the latter comprises a large number of individual meshes and is in this particular embodiment larger, i.e. has larger area, than the first panel 11. The first panel 11 is provided with a first arm 31, which can be a first mesh arm 31, and a third arm 33, which can be a third mesh arm 33, which both extend out from the first panel 11 on a first side (on the left-hand side in FIG. 3) of the first panel 11, and a second arm 32, which can be a second mesh arm 32, and a fourth arm 34, which can be fourth mesh arm 34, which both extend out from the first panel 11 on a second side (on the right- hand side in FIG. 3) of the first panel 11, so that the first and third arms 31, 33 and the second and fourth arms 32, 34 project on opposite sides of the first mesh panel 11. As was discussed above, the first panel 11 and the second mesh panel 12 can have virtually any shape and are in this embodiment divided or separated (but not physically separated) by a waist or midsection 13.

Further, the first arm 31 has a length $L_1$, the second arm 32 has length $L_2$, the third arm 33 has a length $L_3$ and the fourth arm 34 has a length $L_4$. According to the invention, the arm lengths $L_1$, $L_2$, $L_3$ and $L_4$ are relatively long, and depend in practice on the size of the particular breast implant that the mesh support device 10 is intended to support. The size of the mesh support device 10, i.e. the size of the first panel 11 and the size of the second mesh panel 12, depends also on the size of the breast implant that is going to be used together with the support device 10, and here the size of the mesh support device 10 is characterized by widths $W_1$ and $W_2$, respectively.

To achieve the special advantages with a mesh support device 10 according to the invention, the arms 31, 32, 33 and 34 are relatively long, but to not impair neither the user-friendliness nor the manufacturing efficiency should not be excessively long, and according to the present invention their lengths should be chosen such that 30mm$\leq L_1$ $\leq$210 mm, and more preferably 70 mm$\leq L_1 \leq$180mm, and most preferably 110mm $\leq L_1$ $\leq$150mm; and 30mm $\leq L_2$ $\leq$210mm, and more preferably 70mm$\leq L_2$ $\leq$180mm, and most preferably 110mm $\leq L_2$ $\leq$150mm; and 30mm $\leq L_3$ $\leq$210mm, and more preferably 70$\leq$mm $L_3$ $\leq$180mm, and most preferably 110mm$\leq L_3$ $\leq$150mm; and 30mm $\leq L_4$ $\leq$210mm, and more preferably 70mm $\leq L_4$ $\leq$180mm, and most preferably 110mm $\leq L_4$ $\leq$150mm In this particular embodiment, there are four arms 31, 32, 33 and 34 provided at the first panel 11, but other numbers of arms could have been arranged. The first arm 31 and the second arm 32 have typically the same length ($L_1 = L_2$), and the third arm 33 and the fourth arm 34 have typical the same length ($L_3 = L_4$), but it is within the scope of the invention that the all lengths are different ($L_1 \neq L_2 \neq L_3 \neq L_4$) as long as the arms fulfill their respective length intervals.

The third embodiment of a medical support device 10 shown in FIG. 3, has four arms instead of two arms as was the case for the first embodiment and the second embodiment depicted in FIGS. 1*a-c* and FIGS. 2*a-c*, respectively. In FIG. 3 it is further illustrated that according to the invention, an arm can be made from the same piece of material, which can be mesh material, as a first panel, i.e. the arms and the first mesh panel are cut out from the same piece of material, which can be mesh material. This is the case for the first and second arms 31, 32 in the embodiment shown in FIG. 3. To use the same piece of material for the arms and the first panel provides for an efficient manufacturing procedure. The third and fourth arms 33, 34 are, however, instead arranged as separate arms 33, 34, which have been attached, e.g. by sewing, stitching or gluing, at the first panel 11. To arrange arms as separate elements provides for the possibility to have one material in the arms and another, different material in the first mesh panel. The material of the arms can thereby, for example, be chosen to provide for a good strength and/or a good friction locking of the arms within the selected individual meshes, while the material selected for the first panel provides for, e.g., good flexibility and/or tissue integration. However, for manufacturing reasons, for example to provide for an efficient use of material, also separate arms, which are attached, e.g. by sewing, stitching or gluing, to a first panel, can be made from the same type material, but are then not cut out from the same piece of material. For all embodiments of the present invention, arms can either be provided as arms which are integral with a first panel, i.e. are cut out from the same piece of material, or arms can be provided as separate elements, which are attached to a first panel. In the latter case, the arms and the first panel can be made from the same type of material or from different materials. In all cases the material(s) discussed in the section above can be mesh material(s). It can further be seen that the second arm 32 is pointed with one side of the other end of the second arm 32 has been angled; and it can also be seen that the first arm 31 also is pointed with both sides of the other end of the first arm 31 are angled. A pointed other end of an arm can facilitate the threading of the arm through an individual mesh. All arms of all embodiments of the present support device can be made pointed.

FIG. 3 illustrates further that the second mesh panel 12 comprises mesh tabs 41, 42, which consists of a number of individual meshes, where a first mesh tab 41 projects out on a first side (on the left-hand side in FIG. 3) from the general contour of the second mesh panel 12 and a second mesh tab 42 projects out on a second, opposite side (on the right-hand side in FIG. 3) from the general contour of the second mesh panel 12. The arrangement of individual meshes in mesh tabs that project out from opposite sides of the general perimeter of a mesh panel can provide for a receiving space whose shape is well adapted to the shape of breast implant that is to be positioned therein.

The mesh tabs 41, 42 can be made integral with the second mesh panel 12, i.e. the tabs 41, 42 and the second mesh panel 12 are cut out from the same piece of mesh material. As an alternative, it is, however, possible to arrange the mesh tabs 41, 42 as separate elements on the second mesh panel 12. The mesh tabs 41, 41 can then be attached, e.g. by sewing, stitching or gluing, on the second mesh panel 12. To provide individual meshes in mesh tabs 41, 42, which are arranged as separate elements, provide for the possibility to have one mesh material in the mesh tabs 41, 42 and another, different mesh material in the second mesh panel 12. The mesh material of a tab, and consequently the thread material that surrounds the individual meshes, can thereby, for example, be chosen to provide for a good strength and/or a good friction locking of the arms once threaded through an individual mesh, while the material selected for the second mesh panel provides for good flexibility and/or tissue integration. For all embodiments of the present invention, individual meshes can either be provided in a second mesh panel and are thereby located inside the general contour of the second mesh panel, or individual meshes can be provided in mesh tabs, which project out from the general contour of the second mesh panel and which either are integral with the second mesh panel, i.e. the mesh tabs and the second mesh panel are cut out from the same piece of mesh material, or which are arranged as separate elements and are attached to the second mesh panel by, for example, sewing, stitching or gluing. In the latter case, the mesh tabs and the second mesh panel can be made from the same type of mesh material or from different mesh materials.

As stated above, the present invention also relates to a method for positioning and fixating a breast implant in a mesh support device comprising a first panel and second panel, which are configured to be positioned opposite each other and of which at least the second panel is a mesh panel, which consists of a large number of individual meshes, wherein the mesh support device further comprises a first arm arranged at a first side of the first panel and a second arm arranged at a second side of the first panel, the second side being opposite to the first side, which method comprises the steps of:

determining a suitable position for the breast implant between the first panel and the second mesh panel;

based on the determined suitable position, selecting a first one of said large number of individual meshes and thread the first arm through this selected first individual mesh; and based on the determined suitable position, selecting a second one of said large number of individual meshes and threading the second arm through this selected second individual mesh, wherein the selected first individual mesh and the selected second individual mesh are selected such that the breast implant is positioned between the first arm and the second arm.

Each threading step can be preceded by same manipulation of the arm to be threaded. The arm can, for example, folded or rolled along its longitudinal extension, to thereby create a more solid and more pointed arm. To facilitate the threading operation, the arms can also be made more pointed, as was discussed in conjunction with FIG. 3 above. As an alternative or supplement, an arm, i.e. preferably an outer end thereof, can further be provided with a stiffener, which can comprise hardening of the material of the outer end of the arm, e.g. by a heat treatment, or a coating can be arranged on the outer end of the arm, or a small object, such as a rod or pin, can be attached to the outer end of an arm. All of these and similar means and measures provided to stiffen the outer end of an arm are herein encompassed in the term “stiffener”.

Figure 4A:
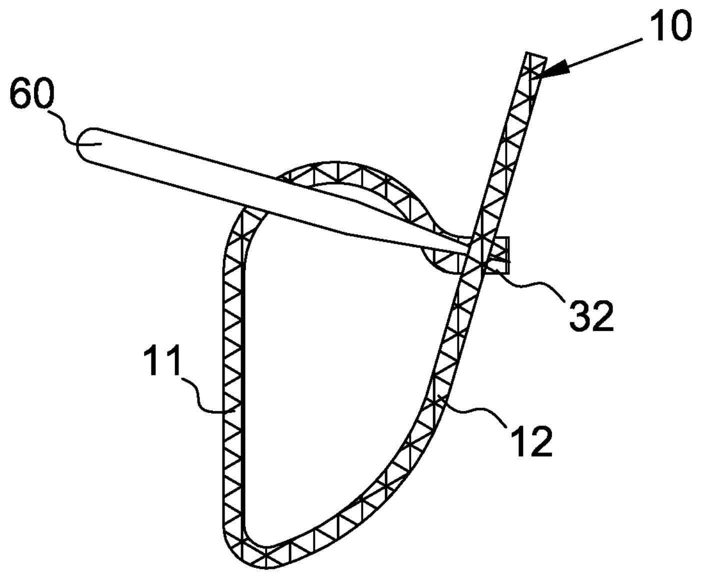
FIG. 4*a* illustrates schematically how a threading device is used to push an arm of a first panel through an individual mesh of a second mesh panel.
Figure 4B:
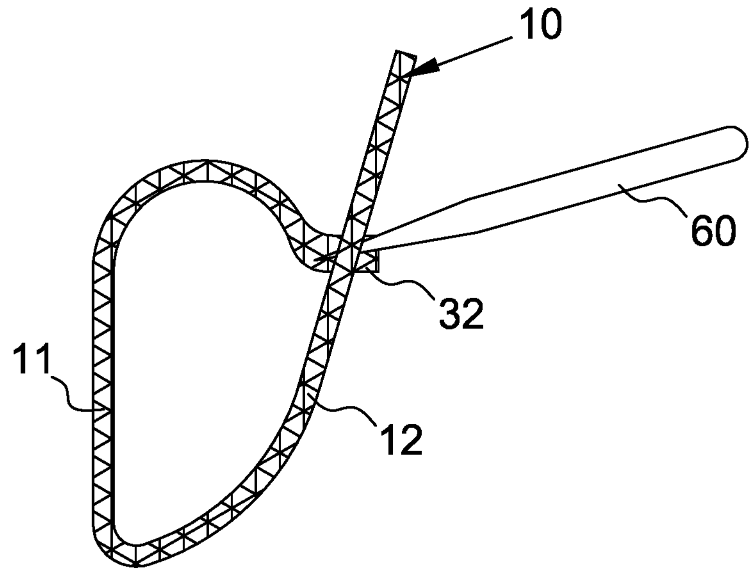
FIG. 4*b* illustrates schematically how a threading device is used to pull an arm of a first panel through an individual mesh of a second mesh panel.

In FIGS. 4*a* and 4*b* it is illustrated that the threading operation can be carried out by the use of a threading device; and more specifically FIG. 4*a* shows a mesh support device 10 having a first mesh panel 11, which comprises an arm 32, and a second mesh panel 12, which consists of a large number of individual meshes, and wherein a threading device 60, which here is exemplified as a pair of forceps 60 and which is used to push the arm 32 through a selected individual mesh of the second mesh panel 12. FIG. 4*b* illustrates a mesh support device 10 having a first mesh panel 11, which comprises an arm 32, and a second mesh panel 12, which consists of a large number of individual meshes, wherein a threading device 60, which here is exemplified as a pair of forceps 60 and which is used to pull the arm 32 through a selected individual mesh of the second mesh panel 12. Thus, FIG. 4*a* and FIG. 4*b* illustrate that the term “threading” encompasses both “pushing” and “pulling”.

Figure 5:
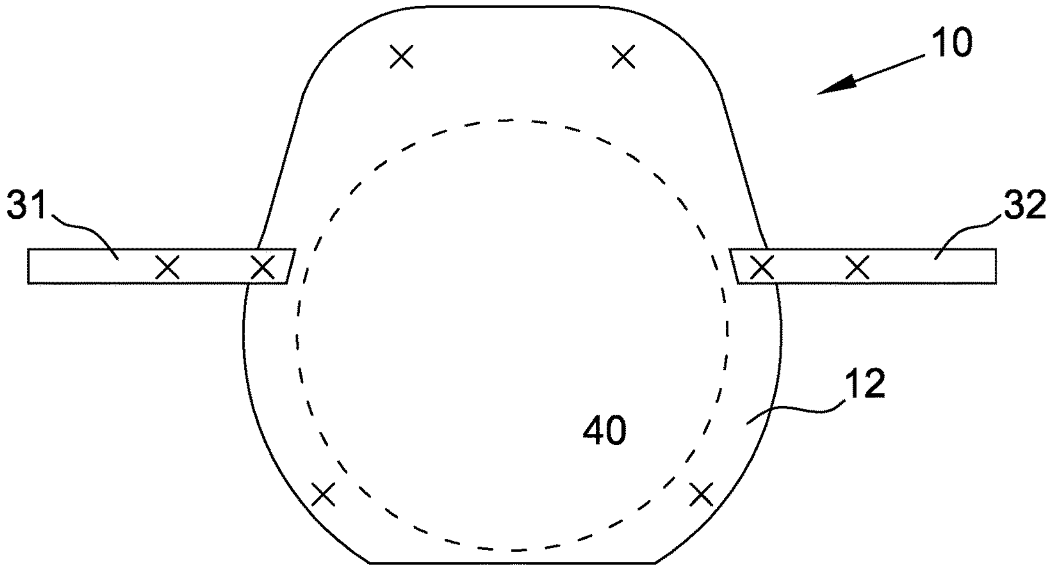
FIG. 5 illustrates schematically a front view of a mesh support device according to the invention with a breast implant placed therein.

FIG. 5 illustrates a front view of a mesh support device 10 with a breast implant 40 in place, and it can in particular be seen that a second mesh panel 12 serves as a front panel and covers the breast implant 40 and that a first arm 31 and a second arm 32, which are arranged at a first panel 11 (not visible in FIG. 5), have been threaded through individual meshes in the second mesh panel 12. The first and second arms 31, 32, which according to the invention are relatively long, can now advantageously be used for securing the mesh support device 10 in a patient’s breast tissue. Further, by selecting the size of mesh support device 10, and in particular by selecting the size of the panel that will serve as front panel, in such a way that extra material is provided around at least parts of the breast implant 40, this extra material can be used to secure, e.g. by stapling, sewing or stitching, the mesh support device 10 in the patient’s breast tissue at, for example, the positions marked with crosses. It can further be noted that when the arms 31, 32 are secured in the breast tissue, the breast implant 40 is simultaneously further fixated within the mesh support device 10, i.e. as a supplement to the fixation that already has been accomplished be pulling the arms 31, 32 fully through the selected individual meshes in the second mesh panel 12, such that the arms 31, 32 are held in place by friction locking created between the respective arm and the inner perimeter of the individual meshes through which the arms have been threaded.

Thus, for all embodiments presented herein, the dimension of an individual mesh is generally much smaller than the width of an arm that is configured to be threaded through the individual mesh. Typically, some manipulation is therefore required to initially force the arm through the selected individual mesh, and the arm can, for example, be gently folded or rolled along its longitudinal axis, to temporarily reduce its transverse extension, before the arms is threaded, i.e. pulled or pushed, through the individual mesh. To provide for a secure and reliable friction locking the first arm can have width in the interval of 5 mm to 30 mm, and also the second arm can have a width in the interval of 5 mm to 30 mm. However, the widths chosen for the first and second arms depend on the size and also shape of the individual meshes. The corresponding widths are applicable if more than two arms are arranged in or at a panel.

As has been mentioned above, the arms of a first panel can be arranged integral with the first panel, i.e. the arms and first mesh panel are cut out from the same piece of material, which can be a mesh material, or the arms can be arranged as separate elements which are attached to the first panel. In the latter case, the arms can be made from the same sort of material as the first panel, or the arms and the first panel can be made from different materials, such that one material is a mesh material or both materials are mesh materials. Similarly, for all embodiments presented herein, a first panel can be made from a first material, which can be a mesh material, and a second mesh panel can be made from a second material, which is different from the first material. In this case, the first panel and the second mesh panel are joined together, e.g. by sewing, at a position that will correspond to a midsection. If, for example, the first panel is intended to constitute the front panel, the first material can be a flexible material that adapts to the convex shape of the front side of a breast implant, while the second material is a material that promotes tissue integration at the backside of the breast implant. Obviously, the opposite applies if the second mesh panel is intended to constitute the front panel, while the first panel is intended to constitute the back panel.

However, as an alternative, which also applies for all embodiments presented herein, a first panel, which is a first mesh panel, and a second mesh panel can be made as an integral unit, which here means that the first mesh panel and the second mesh panel are arranged as one piece of mesh material, i.e. a front panel and a back panel are created by folding the piece of mesh material at a midsection or waist. This latter case, when the first mesh panel and the second mesh panel are made from the same piece of mesh material, provides for a very efficient and material-saving manufacturing, as is illustrated in FIG. 6.

Figure 6:
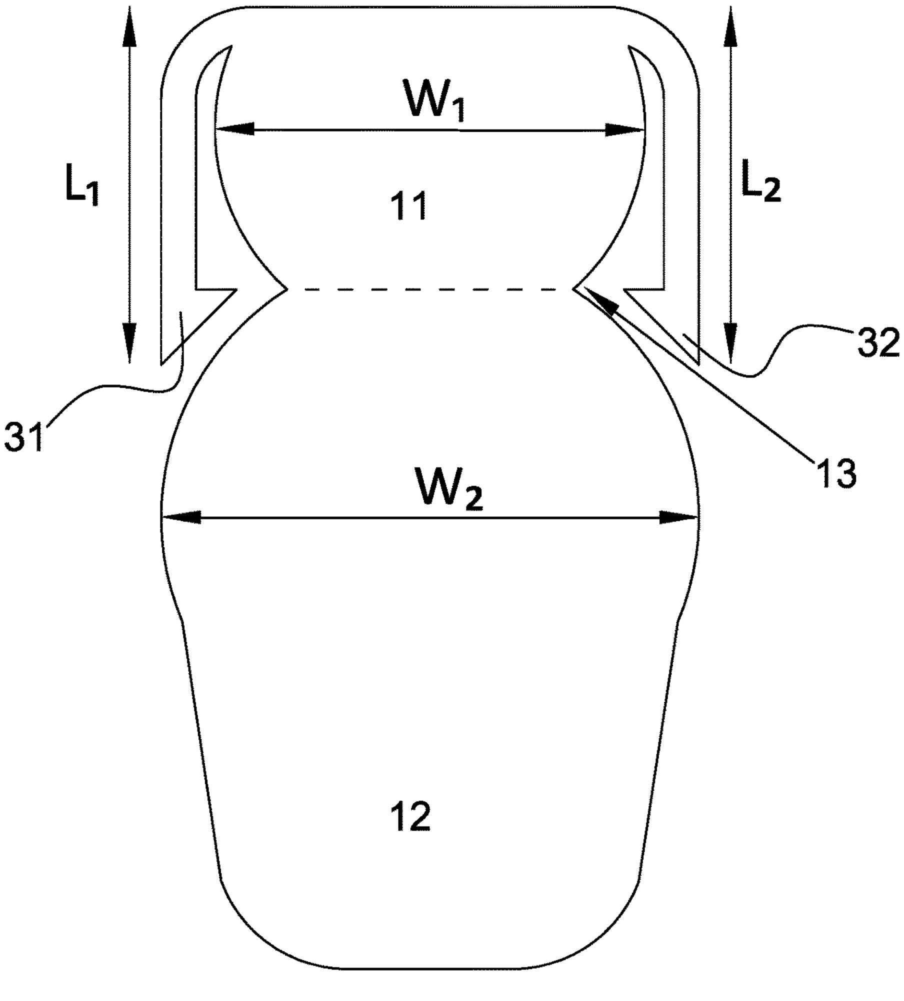
FIG. 6 illustrates schematically a front view of a fourth embodiment of a mesh support device according to the present invention.

FIG. 6 illustrates a fourth embodiment of a mesh support device 10 according to the present invention, where the mesh support device 10 comprises a first panel 11, which here is a first mesh panel 11 and having a largest width Wi, and a second mesh panel 12 having a largest width W2. The first mesh panel 11 comprises a first arm 31, which is configured to be threaded through an individual mesh the second mesh panel 12, and a second arm 32, which is configured to be threaded through an individual mesh of the second mesh panel 12, as has been described before. The first mesh panel 11 and the second mesh panel 12 are cut out from the same piece of mesh material; and to create a receiving space for a breast implant, the mesh support device 10 is folded or bent at the position of a waist or midsection 13. A special feature of the mesh support device 10 shown in FIG. 6 is that also the first and second arms 31, 32 are cut out from the same piece of mesh material, and rather than extending more or less transversally to the general extension of the mesh support device 10 — something which has been the case for the arms described in conjunction with the previous embodiments and figures — the first and second arms 31 of this embodiment extend generally along the first mesh panel 11, to thereby provide for a manufacturing that makes efficient use of the available mesh material. A configuration wherein the first mesh panel, the second mesh panel and the arms are all cut out from the same piece of mesh material can be applied for all embodiments presented herein, and the arms can also be arranged generally along (rather than generally perpendicular to) a first mesh panel for all embodiments presented herein. In one embodiment the first and the second arm are arranged essentially perpendicular to the first and second side respectively. In one embodiment the third and the fourth arm are arranged essentially perpendicular to the first and second side respectively.

A mesh panel of a mesh support device 10 can be made by means of any known knitting or weaving technique, and it is preferred that the mesh for the mesh panel is made by a technique that prevents unraveling of the mesh panel. One example of such a knitting technique is warp-knitting, which is a family of knitting methods in which the yarn zigzags along the length of the fabric, i.e. following adjacent columns of knitting rather than a single row. By using a manufacturing method that prevents, or at least reduces the risk of, unraveling, the mesh support device can be more reliable anchored (e.g. stitched, sewed, sutured or stapled) to the human breast tissue during and after implantation of a breast implant.

In a preferred embodiment, the mesh of a mesh support device 10 is made from a degradable material, and preferably from a bio-degradable material, which means that the material in question can be resorbed by the human body. By using a degradable material, which degrades inside the body, complications that are known to sometimes be associated with permanent mesh products can be avoided. Examples of materials in the fibers or yarns that constitute the mesh of the mesh support device 10 are (a) resorbable polymers with a relatively short degradation time, and non-limiting examples are polymers or copolymers made from the monomer glycolide in pure form, or in combination with paradioxanone, lactide, trimethylene carbonate or caprolactone, or polymers or copolymers made from the monomer paradioxanone in its pure form, or in combination with lactide, trimethylene carbonate or caprolactone; or (b) resorbable polymers with a relative long degradation time, and non-limiting examples are polylactide and polyurethanes, e.g. polyureaurethanes, polyesterurethanes and polycarbonateurethanes; or (c) any combinations thereof.

As indicated above, several materials can be combined in a single mesh support device according to the present invention, and a suitable mesh is commercially available under the tradename TIGR® Matrix Surgical Mesh and is sold by the company Novus Scientific. This mesh, which is described in U.S. Pat. Nos. 9,566,370, 8,083,755 and 8,016,841, comprises two different polymers having different degradation times, and it is believed that the resulting gradual degradation can promote tissue integration of a mesh support device made by this particular mesh. However, although synthetic and degradable materials are believed to be advantageous, a mesh support device according to the present invention can be made from permanent (non-degradable, non-resorbable) synthetic materials or even from biological materials, and any combination thereof Although the present invention has been described with reference to specific embodiments, also shown in the appended drawings, it will be apparent to those skilled in the art that many variations and modifications can be done within the scope of the invention as described in the specification and defined with reference to the claims below.

The invention claimed is:

1. A mesh support device for supporting a breast implant, the mesh support device comprising:

a first panel having a first edge and a second edge opposite the first edge; and a second panel connected to the first panel, the second panel having a first edge and a second edge opposite the first edge of the second panel, the second panel being a mesh panel comprising a plurality of openings; wherein:

the first panel and the second panel are divided or separated by a waist having a width less than a width of the first panel and a width of the second panel;

the first edge of the first panel extends to the first edge of the second panel, and the second edge of the first panel extends to the second edge of the second panel; and the mesh support device further comprises:

a first arm that extends from the first edge of the first panel; and a second arm that extends from the second edge of the first panel; wherein:

the first arm and the second arm extend in substantially opposite directions and are configured to extend across opposite lateral surfaces of the breast implant; and each of the first and second arms is configured to be threaded through respective ones of the plurality of openings upon folding or bending the mesh support device at the waist such that the first panel and the second panel are positioned opposite each other with a receiving space located therebetween.

2. The mesh support device according to claim 1, wherein the first panel is a mesh panel.

3. The mesh support device according to claim 2, wherein the first panel and the second panel are panels that have been cut out from the same piece of mesh material.

4. The mesh support device according to claim 3, wherein also the first and second arms are arms that have been cut out from the same piece of mesh material.

5. The mesh support device according to claim 3, wherein the mesh material is a bio-degradable mesh material.

6. The mesh support device according to claim 1, wherein a length of the first arm and a length of the second arm are each in a range of 70 mm to 180 mm, inclusive.

7. The mesh support device according to claim 1, wherein a length of the first arm and a length of the second arm are each in a range of 110 mm to 150 mm, inclusive.

8. The mesh support device according to claim 1, wherein a width of the first arm and a width of the second arm are larger than a maximum dimension of the respective ones of the openings such that a friction locking is created once the first arm and the second arm have been threaded through the respective ones of the openings.

9. The mesh support device according to claim 1, wherein the first panel is made from a first material and the second panel is made from a second material different from the first material.

10. The mesh support device according to claim 9, wherein the first and second materials are bio-degradable materials having different degradation times.

11. The mesh support device according to claim 1, wherein an outer end of the first arm and/or an outer end of the second arm is pointed.

12. The mesh support device according to claim 1, wherein an outer end of the first arm and/or an outer end of the second arm comprises a stiffener.

13. The mesh support device according to claim 1, wherein an area and/or a width of the second panel is larger than an area and/or a width of the first panel.

14. The mesh support device according to claim 1, wherein a length of the first arm and a length of the second arm are each in a range of 30 mm to 210 mm, inclusive.

15. The mesh support device according to claim 1, wherein the first panel has a linear third edge extending parallel to the directions in which the first and second arms extend.

16. The mesh support device according to claim 15, wherein an edge of the first arm and an edge of the second arm are colinear with the linear third edge.

17. The mesh support device according to claim 1, wherein:

a length of the second panel is greater than a length of the first panel; and the waist is configured to engage a bottom of the breast implant such that the first arm and the second arm are configured to extend across an upper half of the breast implant.

18. The mesh support device according to claim 1, further comprising a third arm extending from the first panel and a fourth arm extending from the first panel, the third and fourth arms extending in a direction away from the first arm and the second arm.

* * * * *